United States Patent
Linehan et al.

(10) Patent No.: US 12,318,600 B2
(45) Date of Patent: Jun. 3, 2025

(54) STERILE CONNECTOR AND CANNULA ASSEMBLY

(71) Applicant: CARDIACASSIST, INC., Pittsburgh, PA (US)

(72) Inventors: Michael J. Linehan, Pittsburgh, PA (US); Anthony McCoppin, Blawnox, PA (US); John C. Marous, III, Pittsburgh, PA (US); Robert G. Svitek, Freeport, PA (US)

(73) Assignee: CARDIACASSIST, INC.

( * ) Notice: Subject to any disclaimer, the term of this patent is extended or adjusted under 35 U.S.C. 154(b) by 1182 days.

(21) Appl. No.: 16/951,451

(22) Filed: Nov. 18, 2020

(65) Prior Publication Data
US 2021/0085844 A1   Mar. 25, 2021

Related U.S. Application Data

(63) Continuation of application No. PCT/US2019/036728, filed on Jun. 12, 2019.
(Continued)

(51) Int. Cl.
*A61M 60/113* (2021.01)
*A61M 39/12* (2006.01)
(Continued)

(52) U.S. Cl.
CPC .......... *A61M 60/113* (2021.01); *A61M 39/12* (2013.01); *A61M 60/205* (2021.01); *A61M 60/38* (2021.01); *A61M 60/859* (2021.01)

(58) Field of Classification Search
CPC .. A61M 60/113; A61M 39/12; A61M 60/205; A61M 60/38; A61M 60/859;
(Continued)

(56) References Cited

U.S. PATENT DOCUMENTS 3,707,972 A   1/1973 Villari et al.
4,146,034 A * 3/1979 Gupta ............... A61M 39/12
                                                128/207.14
(Continued)

FOREIGN PATENT DOCUMENTS

EP   1674123 A1   6/2006

OTHER PUBLICATIONS

International Preliminary Report on Patentability, dated Jun. 12, 2019 for International Application No. PCT/US2019/036728.
(Continued)

*Primary Examiner* — Nathan R Price
*Assistant Examiner* — Fatimata Sahra Diop
(74) *Attorney, Agent, or Firm* — Seager, Tufte & Wickhem LLP

(57) ABSTRACT

A connector has a hollow body having a first open end spaced apart from a second open end with a lumen extending between the first and second open ends. At least one channel extends through a sidewall of the body and is recessed from a terminal surface of the first open end. The first open end is sized to be received within an open end of a first tubing. When the first open end is partially inserted into the open end of the first tubing, the at least one channel and a terminal surface of the open end of the first tubing define an opening positioned so that fluid passes through the opening into or out of the lumen. When the first open end is fully inserted into the first tube, the at least one channel is covered by an inner surface of the first tubing to cover the opening.

14 Claims, 12 Drawing Sheets

Related U.S. Application Data

(60) Provisional application No. 62/684,063, filed on Jun. 12, 2018.

(51) Int. Cl.
*A61M 60/205* (2021.01)
*A61M 60/38* (2021.01)
*A61M 60/859* (2021.01)

(58) Field of Classification Search
CPC .. A61M 1/3659; A61M 1/3666; A61M 39/10; A61M 39/16
See application file for complete search history.

(56) References Cited

U.S. PATENT DOCUMENTS

| | | | | |
|---|---|---|---|---|
| 4,162,566 A | * | 7/1979 | Webb | F25B 41/40 |
| | | | | 29/890.035 |
| 4,929,236 A | * | 5/1990 | Sampson | A61M 39/12 |
| | | | | 604/905 |
| 4,946,445 A | * | 8/1990 | Lynn | A61M 39/04 |
| | | | | 604/905 |
| 6,158,784 A | * | 12/2000 | Lavender | F16L 33/30 |
| | | | | 285/259 |
| 2007/0249197 A1 | | 10/2007 | Spranger et al. | |
| 2008/0092901 A1 | | 4/2008 | Kang | |
| 2010/0154800 A1 | | 6/2010 | Chang et al. | |
| 2011/0082431 A1 | | 4/2011 | Burgess et al. | |
| 2012/0022457 A1 | | 1/2012 | Silver | |
| 2012/0316539 A1 | | 12/2012 | Villasana | |
| 2017/0363240 A1 | | 12/2017 | Ira et al. | |

OTHER PUBLICATIONS

International Search Report, dated Jun. 12, 2019 for International Application No. PCT/US2019/036728.

Written Opinion, dated Jun. 12, 2019 for International Application No. PCT/US2019/036728.

* cited by examiner

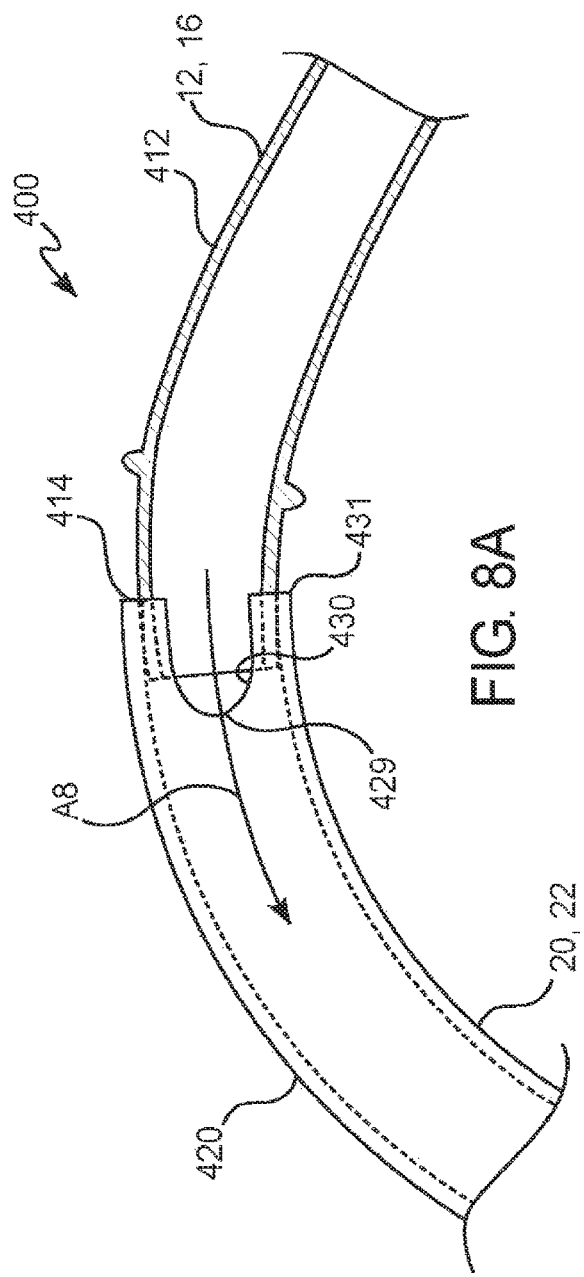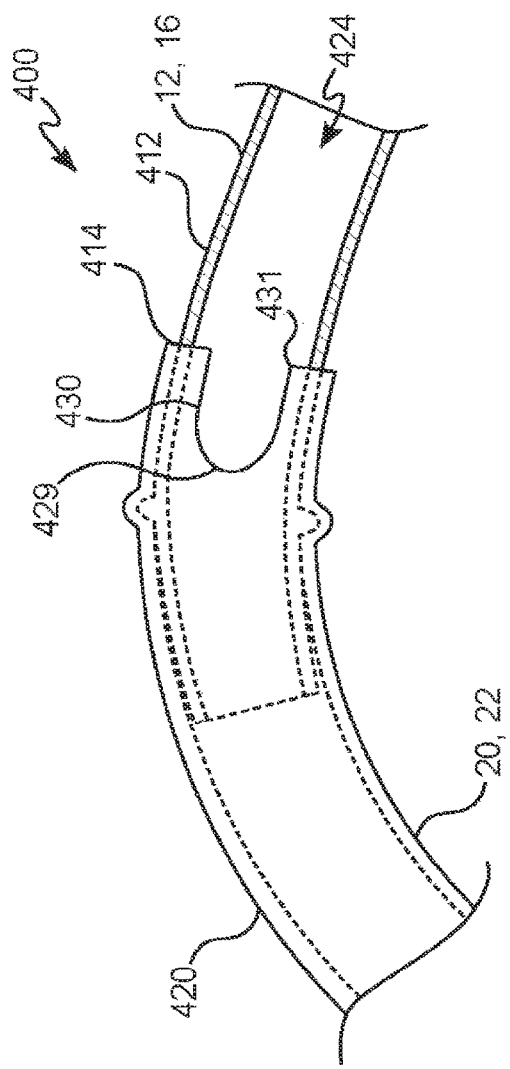

STERILE CONNECTOR AND CANNULA ASSEMBLY

CROSS-REFERENCE TO RELATED APPLICATIONS

This application is a continuation of International Application No. PCT/US2019/036728, filed Jun. 12, 2019, which claims priority to U.S. Provisional Application No. 62/684,063, filed Jun. 12, 2018, the disclosures of which are hereby incorporated in its entirety.

BACKGROUND OF THE DISCLOSURE

Field of the Disclosure

The present disclosure relates to a connector for connecting ends of separate fluid conduits together, which can be used with a cannula assembly, such as a cannula assembly connected to a pump for removing and reintroducing blood to a patient, and, in particular, to a connector that creates a sterile wet-to-wet connection between portions of the cannula assembly.

Description of Related Art

Current therapy for providing assistance to a patient's heart may involve the use of complex cardiac assist systems. As will be appreciated by those skilled in the art, portions of surgical tubing used in such cardiac assist systems must be connected together in a sterile and safe manner, while avoiding introducing contaminants and/or air bubbles into the system. Currently, such sterile connections are formed using a wet-to-wet connection technique, in which one user holds an end of the sections of tubing to be connected together in each hand. The user slowly brings the ends together, while a second user continuously dispenses fluid from a syringe over the ends as the connection is being formed until a seal is made. In other examples, a connection between ends of different sections of tubing can be formed using a priming tray.

Such connectors and connection techniques can be complex and often require at least two people to form the connection. Such techniques can also be messy, allowing a large volume of fluid to spill over a working area as a wet-to-wet connection is being formed. Using a priming tray can also be cumbersome. Accordingly, there is a need in the art for an improved connector and connection technique for making a sterile connection between portions of surgical tubing in a cardiac assist system.

SUMMARY OF THE DISCLOSURE

In view of the foregoing, there is a need for improved connectors and connection techniques, which can be performed easily by one person. Such connectors should be capable of quickly and easily connecting pieces of surgical tubing. In comparison, conventional systems are not easily connected and disconnected and thus are more difficult to prime and to change components when complications occur. Systems configured to address these issues are discussed herein According to some non-limiting embodiments or aspects of the present disclosure, a connector may have a hollow body having a first open end spaced apart from a second open end with a lumen extending between the first open end and the second open end. The connector further may have at least one channel extending through a sidewall of the hollow body. The at least one channel may be recessed axially from a terminal surface of the first open end. The first open end of the connector may be sized to be received within an open end of a first tubing. When the first open end is partially inserted into the open end of the first tubing, the at least one channel and a terminal surface of the open end of the first tubing may define an opening positioned so that fluid passes through the opening into or out of the lumen. When the first open end is fully inserted into the open end of the first tubing, the at least one channel may be covered by an inner surface of the first tubing to cover the opening.

According to some non-limiting embodiments or aspects of the present disclosure, the at least one channel may be U-shaped. The at least one channel may have a curved end and a pair of sides connecting the curved end to the terminal surface of the first open end. A width of the at least one channel may be from 60% to 100% of a length of the at least one channel. An area of the at least one opening, when the first open end of the connector is partially inserted into the open end of the first tubing, may be from 15.0 mm$^2$ to 60.0 mm$^2$. An area of the at least one opening, when the first open end of the connector is partially inserted into the open end of the first tubing, may be from 20% to 75% of a cross-sectional area of the first tube.

According to some non-limiting embodiments or aspects of the present disclosure, the first open end may have a first tapered portion configured to be inserted in the open end of the first tubing. The first tapered portion may have one or more of a luer connector, a threaded connector, and a snap fit connector. The second open end may be sized to be received within an open end of a second tubing. The second open end may have a second tapered portion configured to be inserted in the open end of the second tubing. The second tapered portion may have one or more of a luer connector, a threaded connector, and a snap fit connector.

According to some non-limiting embodiments or aspects of the present disclosure, at least one ridge or barb may protrude outward relative to an outer surface of the hollow body. The at least one ridge or barb may be a plurality of ridges or barbs axially spaced from each other along a length of the hollow body between the first open end and the second open end. A gripping portion may be provided between the first open end and the second open end. The gripping portion may have a first end having a first diameter, a second end having a second diameter, and an intermediate portion between the first end and the second end, the intermediate portion having a third diameter less than the first diameter and the second diameter.

According to some non-limiting embodiments or aspects of the present disclosure, a cannula assembly for providing a sterile connection between tubing portions of the assembly may have a first tubing portion with an open end, a second tubing portion with an open end; and a connector having a hollow body with a first open end spaced apart from a second open end and a lumen extending between the first open end and the second open end. The first open end may be sized to be received within the open end of the first tubing. The second open end may be sized to be received within the open end of the second tubing. At least one channel may extend through a sidewall of the hollow body. The at least one channel may be recessed axially from a terminal surface of the first open end. When the first open end is partially inserted into the open end of the first tubing, the at least one channel and a terminal surface of the open end of the first tubing may define an opening positioned so that fluid passes through the opening into or out of the lumen. When the first open end is fully inserted into the open end of the first tubing, the at least one channel may be covered by an inner surface of the first tubing to cover the opening.

According to some non-limiting embodiments or aspects of the present disclosure, a tubing assembly may have a first tubing portion with an open end, and a connector having a hollow body with a first open end spaced apart from a second open end and a lumen extending between the first open end and the second open end. The first open end may be sized to be received within the open end of the first tubing. At least one channel may extend through a sidewall of the hollow body. The at least one channel may be recessed axially from a terminal surface of the first open end. When the first open end is partially inserted into the open end of the first tubing, the at least one channel and a terminal surface of the open end of the first tubing may define an opening positioned so that fluid passes through the opening into or out of the lumen. When the first open end is fully inserted into the open end of the first tubing, the at least one channel may be covered by an inner surface of the first tubing to cover the opening.

According to some non-limiting embodiments or aspects of the present disclosure, a method of providing a sterile connection between tubing joined by a connector may include partially inserting an open end of a first tubing into a first open end of the connector, thereby forming a lumen extending through the first tubing and the connector. The connector may have at least one channel extending through a sidewall of the connector and recessed from a terminal surface of the first open end. The at least one channel and a terminal surface of the open end of the first tubing may define at least one opening positioned so that fluid passes through the at least one opening into or out of the lumen. The method may further include delivering a fluid into the lumen defined by the connected first tubing and the connector such that air present in the lumen escapes from the lumen through the at least one opening.

According to some non-limiting embodiments or aspects of the present disclosure, delivering the fluid into the lumen may include delivering the fluid until the lumen is filled with the fluid. After the lumen is filled with the fluid, the method may further include inserting the first open end of the connector into the open end of the first tubing such that an inner surface of the first tubing covers the at least one opening.

According to some non-limiting embodiments or aspects of the present disclosure, delivering the fluid may include filling the lumen through the at least one opening. Filling the lumen through the at least one opening may include dispensing a stream of the fluid from a syringe into the at least one opening. Delivering the fluid into the lumen may include releasing a clamp of a patient line connected to the first tubing, such that fluid from the patient line passes into the first tubing, thereby expelling the air from the first tubing through the at least one opening.

Further embodiments or aspects are disclosed in the following enumerated clauses.

Clause 1. A connector comprising: a hollow body having a first open end spaced apart from a second open end with a lumen extending between the first open end and the second open end; and at least one channel extending through a sidewall of the hollow body, the at least one channel being recessed axially from a terminal surface of the first open end, wherein the first open end is sized to be received within an open end of a first tubing, wherein, when the first open end is partially inserted into the open end of the first tubing, the at least one channel and a terminal surface of the open end of the first tubing define an opening positioned so that fluid passes through the opening into or out of the lumen, and wherein, when the first open end is fully inserted into the open end of the first tubing, the at least one channel is covered by an inner surface of the first tubing to cover the opening.

Clause 2. The connector of clause 1, wherein the at least one channel is U-shaped.

Clause 3. The connector of clause 1 or 2, wherein the at least one channel has a curved end and a pair of sides connecting the curved end to the terminal surface of the first open end.

Clause 4. The connector of any of clauses 1-3, wherein a width of the at least one channel is from 60% to 100% of a length of the at least one channel.

Clause 5. The connector of any of clauses 1-4, wherein an area of the at least one opening, when the first open end of the connector is partially inserted into the open end of the first tubing, is from 15.0 mm$^2$ to 60.0 mm$^2$.

Clause 6. The connector of any of clauses 1-5, wherein an area of the at least one opening, when the first open end of the connector is partially inserted into the open end of the first tubing, is from 20% to 75% of a cross-sectional area of the first tube.

Clause 7. The connector of any of clauses 1-6, wherein the first open end comprises a first tapered portion configured to be inserted in the open end of the first tubing.

Clause 8. The connector of any of clauses 1-7, wherein the first tapered portion comprises one or more of a luer connector, a threaded connector, and a snap fit connector.

Clause 9. The connector of any of clauses 1-8, wherein the second open end is sized to be received within an open end of a second tubing.

Clause 10. The connector of any of clauses 1-9, wherein the second open end comprises a second tapered portion configured to be inserted in the open end of the second tubing.

Clause 11. The connector of any of clauses 1-10, wherein the second tapered portion comprises one or more of a luer connector, a threaded connector, and a snap fit connector.

Clause 12. The connector of any of clauses 1-11, further comprising at least one ridge or barb protruding outward relative to an outer surface of the hollow body.

Clause 13. The connector of any of clauses 1-12, wherein the at least one ridge or barb is a plurality of ridges or barbs axially spaced from each other along a length of the hollow body between the first open end and the second open end.

Clause 14. The connector of any of clauses 1-13, further comprising a gripping portion between the first open end and the second open end, the gripping portion having a first end having a first diameter, a second end having a second diameter, and an intermediate portion between the first end and the second end, the intermediate portion having a third diameter less than the first diameter and the second diameter.

Clause 15. A cannula assembly for providing a sterile connection between tubing portions of the assembly, the cannula assembly comprising: a first tubing portion comprising an open end; a second tubing portion comprising an open end; and a connector having a hollow body with a first open end spaced apart from a second open end and a lumen extending between the first open end and the second open end, wherein the first open end is sized to be received within the open end of the first tubing, wherein the second open end is sized to be received within the open end of the second tubing, wherein at least one channel extends through a sidewall of the hollow body, the at least one channel being recessed axially from a terminal surface of the first open end, wherein, when the first open end is partially inserted into the open end of the first tubing, the at least one channel and a terminal surface of the open end of the first tubing define an opening positioned so that fluid passes through the opening into or out of the lumen, and wherein, when the first open end is fully inserted into the open end of the first tubing, the at least one channel is covered by an inner surface of the first tubing to cover the opening.

Clause 16. The cannula assembly of clause 15, wherein the at least one channel is U-shaped.

Clause 17. The cannula assembly of clause 15 or 16, wherein the at least one channel has a curved end and a pair of sides connecting the curved end to the terminal surface of the first open end.

Clause 18. The cannula assembly of any of clauses 15-17, wherein a width of the at least one channel is from 60% to 100% of a length of the at least one channel.

Clause 19. The cannula assembly of any of clauses 15-18, wherein an area of the at least one opening, when the first open end of the connector is partially inserted into the open end of the first tubing, is from 15.0 mm$^2$ to 60.0 mm$^2$.

Clause 20. The cannula assembly of any of clauses 15-19, wherein an area of the at least one opening, when the first open end of the connector is partially inserted into the open end of the first tubing, is from 20% to 75% of a cross-sectional area of the first tube.

Clause 21. The cannula assembly of any of clauses 15-20, wherein the first open end comprises a first tapered portion configured to be inserted in the open end of the first tubing.

Clause 22. The cannula assembly of any of clauses 15-21, wherein the first tapered portion comprises one or more of a luer connector, a threaded connector, and a snap fit connector.

Clause 23. The cannula assembly of any of clauses 15-22, wherein the second open end comprises a second tapered portion configured to be inserted in the open end of the second tubing.

Clause 24. The cannula assembly of any of clauses 15-23, wherein the second tapered portion comprises one or more of a luer connector, a threaded connector, and a snap fit connector.

Clause 25. The cannula assembly of any of clauses 15-24, further comprising at least one ridge or barb protruding outward relative to an outer surface of the hollow body.

Clause 26. The cannula assembly of any of clauses 15-25, wherein the at least one ridge or barb is a plurality of ridges or barbs axially spaced from each other along a length of the hollow body between the first open end and the second open end.

Clause 27. The cannula assembly of any of clauses 15-26, wherein the connector further comprises a gripping portion between the first open end and the second open end, the gripping portion having a first end having a first diameter, a second end having a second diameter, and an intermediate portion between the first end and the second end, the intermediate portion having a third diameter less than the first diameter and the second diameter.

Clause 28. A tubing assembly comprising: a first tubing portion comprising an open end; and a connector having a hollow body with a first open end spaced apart from a second open end and a lumen extending between the first open end and the second open end, wherein the first open end is sized to be received within the open end of the first tubing, wherein at least one channel extends through a sidewall of the hollow body, the at least one channel being recessed axially from a terminal surface of the first open end, wherein, when the first open end is partially inserted into the open end of the first tubing, the at least one channel and a terminal surface of the open end of the first tubing define an opening positioned so that fluid passes through the opening into or out of the lumen, and wherein, when the first open end is fully inserted into the open end of the first tubing, the at least one channel is covered by an inner surface of the first tubing to cover the opening.

Clause 29. The tubing assembly of clause 28, wherein the at least one channel is U-shaped.

Clause 30. The tubing assembly of clause 28 or 29, wherein the at least one channel has a curved end and a pair of sides connecting the curved end to the terminal surface of the first open end.

Clause 31. The tubing assembly of any of clauses 15-30, wherein a width of the at least one channel is from 60% to 100% of a length of the at least one channel.

Clause 32. The tubing assembly of any of clauses 15-31, wherein an area of the at least one opening, when the first open end of the connector is partially inserted into the open end of the first tubing, is from 15.0 mm$^2$ to 60.0 mm$^2$.

Clause 33. The tubing assembly of any of clauses 15-32, wherein an area of the at least one opening, when the first open end of the connector is partially inserted into the open end of the first tubing, is from 20% to 75% of a cross-sectional area of the first tube.

Clause 34. The tubing assembly of any of clauses 15-33, wherein the first open end comprises a first tapered portion configured to be inserted in the open end of the first tubing.

Clause 35. The tubing assembly of any of clauses 15-34, wherein the first tapered portion comprises one or more of a luer connector, a threaded connector, and a snap fit connector.

Clause 36. The tubing assembly of any of clauses 15-35, further comprising at least one ridge or barb protruding outward relative to an outer surface of the hollow body.

Clause 37. The tubing assembly of any of clauses 15-36, wherein the at least one ridge or barb is a plurality of ridges or barbs axially spaced from each other along a length of the hollow body between the first open end and the second open end.

Clause 38. The tubing assembly of any of clauses 15-37, wherein the connector further comprises a gripping portion between the first open end and the second open end, the gripping portion having a first end having a first diameter, a second end having a second diameter, and an intermediate portion between the first end and the second end, the intermediate portion having a third diameter less than the first diameter and the second diameter.

Clause 39. A method of providing a sterile connection between tubing joined by a connector, the method comprising: partially inserting an open end of a first tubing into a first open end of the connector, thereby forming a lumen extending through the first tubing and the connector, wherein the connector has at least one channel extending through a sidewall of the connector and recessed from a terminal surface of the first open end, and wherein the at least one channel and a terminal surface of the open end of the first tubing define at least one opening positioned so that fluid passes through the at least one opening into or out of the lumen; and delivering a fluid into the lumen defined by the connected first tubing and the connector such that air present in the lumen escapes from the lumen through the at least one opening.

Clause 40. The method of clause 39, wherein delivering the fluid into the lumen comprises delivering the fluid until the lumen is filled with the fluid.

Clause 41. The method of clause 39 or 40, further comprising, after the lumen is filled with the fluid, inserting the first open end of the connector into the open end of the first tubing, such that an inner surface of the first tubing covers the at least one opening.

Clause 42. The method of any of clauses 39-41, wherein delivering the fluid comprises filling the lumen through the at least one opening.

Clause 43. The method of any of clauses 39-42, wherein filling the lumen through the at least one opening comprises dispensing a stream of the fluid from a syringe into the at least one opening.

Clause 44. The method of any of clauses 39-43, wherein delivering the fluid into the lumen comprises releasing a clamp of a patient line connected to the first tubing, such that fluid from the patient line passes into the first tubing, thereby expelling the air from the first tubing through the at least one opening.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

Some of the advantages and features of the preferred aspects or embodiments have been summarized hereinabove. These aspects or embodiments, along with other potential aspects or embodiments will become apparent to those skilled in the art when referencing the following drawings in conjunction with the detailed descriptions as they relate to the figures.

FIGS. 8A and 8B are a schematic drawings of another example of a connection between tubing portions of a cannula assembly, according to some non-limiting embodiments or aspects of the disclosure;

DETAILED DESCRIPTION

Figure 1:
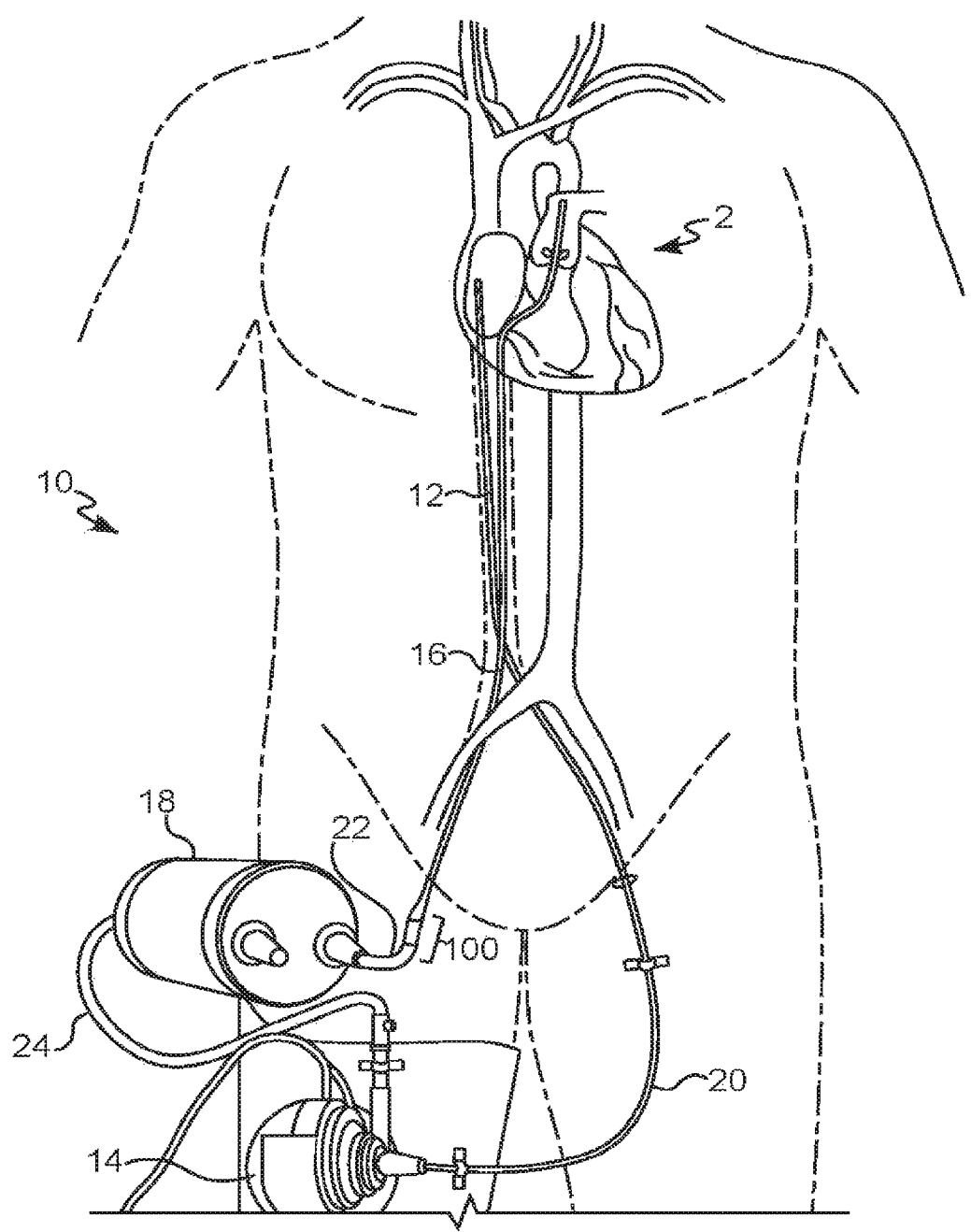
FIG. 1 is a schematic drawing of a cardiac assist system according to some non-limiting embodiments or aspects of the disclosure.

As used in the specification and the claims, the singular form of "a", "an", and "the" include plural referents unless the context clearly dictates otherwise.

For purposes of the description hereinafter, the terms "upper", "lower", "right", "left", "vertical", "horizontal", "top", "bottom", "lateral", "longitudinal", and derivatives thereof shall relate to the components as they are oriented in the drawing figures.

When used in relation to surgical tubing and cannulas of a cannula assembly, the term "distal" refers to a portion of the tubing or cannula closest to the patient. For example, a distal end of a cannula is the end of the cannula inserted into the patient's vasculature.

The term "proximal" refers to an end of tubing or a cannula that is opposite the distal end. In some cases, the proximal end of the cannula or tubing is configured to be connected to a medical device, such as a pump or oxygenator.

All numbers and ranges used in the specification and claims are to be understood as being modified in all instances by the term "about". By "about" is meant plus or minus twenty-five percent of the stated value, such as plus or minus ten percent of the stated value. However, this should not be considered as limiting to any analysis of the values under the doctrine of equivalents.

Unless otherwise indicated, all ranges or ratios disclosed herein are to be understood to encompass the beginning and ending values and any and all subranges or subratios subsumed therein. For example, a stated range or ratio of "1 to 10" should be considered to include any and all subranges or subratios between (and inclusive of) the minimum value of 1 and the maximum value of 10; that is, all subranges or subratios beginning with a minimum value of 1 or more and ending with a maximum value of 10 or less. The ranges and/or ratios disclosed herein represent the average values over the specified range and/or ratio.

The terms "first", "second", and the like are not intended to refer to any particular order or chronology, but refer to different conditions, properties, or elements.

The term "at least" is synonymous with "greater than or equal to".

As used herein, "at least one of" is synonymous with "one or more of". For example, the phrase "at least one of A, B, and C" means any one of A, B, or C, or any combination of any two or more of A, B, or C. For example, "at least one of A, B, and C" includes one or more of A alone; or one or more B alone; or one or more of C alone; or one or more of A and one or more of B; or one or more of A and one or more of C; or one or more of B and one or more of C; or one or more of all of A, B, and C.

The term "includes" is synonymous with "comprises".

As used herein, the terms "parallel" or "substantially parallel" mean a relative angle as between two objects (if extended to theoretical intersection), such as elongated objects and including reference lines, that is from 0° to 5°, or from 0° to 3°, or from 0° to 2°, or from 0° to 1°, or from 0° to 0.5°, or from 0° to 0.25°, or from 0° to 0.1°, inclusive of the recited values.

As used herein, the terms "perpendicular" or "substantially perpendicular" mean a relative angle as between two objects at their real or theoretical intersection is from 85° to 90°, or from 87° to 90°, or from 88° to 90°, or from 89° to 90°, or from 89.5° to 90°, or from 89.75° to 90°, or from 89.9° to 90°, inclusive of the recited values.

It is to be understood, however, that the disclosure may assume alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting.

With reference to the figures, the present disclosure is generally directed to connectors 100, 200, 300, 400, 900 and connection methods. The connectors 100, 200, 300, 400, 900 and methods can be used for providing a sterile connection between surgical tubing and cannulas of a cardiac assist system 10 in a safe and efficient manner. In some examples, the connectors 100, 200, 300, 400, 900 are separable connectors mounted or connected to portions of a cannula assembly or network of surgical tubing. For example, portions of the connectors 100, 200, 300, 400, 900 could be attached to portions of a cannula assembly using a biocompatible adhesive, by being molded together with the tubing of the cannula assembly, or by use of a fastener or other mechanical connection device. In other examples, portions of the cannula assembly can be formed to include features of the sterile connection described herein to form the sterile connection between the portions of the cannula assembly. Unlike other types of connectors, the connectors 100, 200, 300, 400, 900 disclosed herein can be performed easily by a single user (e.g., a clinician or another trained medical professional). The connectors 100, 200, 300, 400, 900 are also configured to allow air to be removed from the system prior to sealing the connection so that air bubbles are not delivered to the patient.

With reference to FIG. 1, the cardiac assist system 10 is configured to provide cardiac assistance for a patient's heart 2, such as by bypassing the left and/or right ventricle, to provide oxygenated blood to the arterial system via the femoral, axillary, or the pulmonary artery. One example of a cardiac assist system 10 which can be adapted for use with the connectors 100, 200, 300, 400, 900 of the present disclosure is disclosed in U.S. Pat. No. 8,550,973 to Magovern et al., which is incorporated by reference in its entirety. Another cardiac assist system 10 and a method of applying the cardiac assist system 10 to a patient are disclosed in U.S. Pat. No. 8,562,519 to Smith et al., which is also incorporated by reference herein in its entirety. Another cardiac assist system 10 is disclosed in U.S. Pat. No. 6,808,508 to Zafirelis, et al., which is discussed hereinabove, and is also incorporated by reference herein in its entirety. A further example of a cardiac assist system 10 which includes a cannula system, blood pump, and patient harness is disclosed in PCT Publication No. WO 2016/161114 to Svitek et al., which is also incorporated by reference herein in its entirety.

In accordance with some non-limiting embodiments or aspects, the cardiac assist system 10 shown in FIG. 1 includes a drainage cannula 12 that is adapted to extend from the right atrium of the patient's heart 2 in fluid communication with a pump 14 to provide blood to the pump 14. The cardiac assist system 10 also includes a femoral or pulmonary artery cannula 16. The cannulas 12, 16 are connected to the pump 14 and an oxygenator 18, respectively, via surgical tubing 20, 22. Dimensions of the cannulas 12, 16 and surgical tubing 20, 22 are dependent upon a desired fluid flow rate through the lumen 124 (shown in FIG. 2) of the corresponding connection between the cannulas and tubing. For example, the cannulas 12, 16 can have an inner diameter of about 9.5 mm±0.2 mm (0.370 inch to 0.385 inch) and an outer diameter from about 14.3 mm±0.2 mm (0.445 inch to 0.475 inch). The surgical tubing 20, 22 can have an inner diameter of 9.5 mm±0.2 mm (⅜ inch) and an outer diameter of 14.3 mm (0.563 inch).

In some non-limiting embodiments or aspects, the cannula 16 can be at least 17 cm in length when configured for insertion into the femoral artery and at least 70 cm in length when configured for insertion into the pulmonary artery, and adapted to extend from the patient's groin to the pulmonary artery of the patient to provide blood to the pulmonary artery for right ventricular support. The cannula 16 can be a dual lumen cannula in the internal jugular vein or a surgical cannula connected directly to the heart 2. The cannula 16 can be a steerable cannula with a steerable mechanism to control the position and shape of the cannula body. Further, the cannula 16 can have a balloon tip to enable self-direction and placement into a flow-directed vessel. An additional lumen can enable placement of additional wires or clot removal devices into the pulmonary artery or vessel. Further, if the cannula 16 is a dual lumen cannula, a transition taper between the side holes on the cannula body can have cut-outs to enable strain relief during placement or manipulation or curving of the cannula around a tortuous anatomy. Finally, a coating on the tip of the cannula 16 can enable radiopacity for placement and position determination. In some aspects, the cannula 16 can be the cannula described in U.S. Pat. No. 9,168,352 to Kelly et al.

The pulmonary artery cannula 16 is in fluid communication with the pump 14 via the tubing 20, whereby the heart's right ventricle is essentially bypassed by draining the right atrium and pumping blood into the pulmonary artery, thereby allowing the right ventricle of the patient to rest and enable right ventricular support. The cannula 16 and the tubing 20 may be connected together via any of the connectors 100, 200, 300, 400, 900 described herein. Preferably, the pump 14 is a ventricular assist pump, such as a centrifugal, axial, mixed, or roller pump, as is known in the art, that produces adequate flow rates through the system 10 to achieve desired therapeutic results (e.g., either cardiac assist or right ventricular bypass). A suitable pump 14 for use with the above-described system 10 is disclosed in U.S. Pat. No. 6,808,508 to Zafirelis et al.

The system 10 can also include an oxygenator 18 in fluid communication with the pump 14 and the pulmonary artery cannula 16. A connection between the oxygenator 18 and the pump 14, and the oxygenator 18 and the pulmonary artery cannula 16 can be made using any of the connectors 100, 200, 300, 400, 900 described herein. The oxygenator 18 receives blood pumped by the pump 14, oxygenates the blood, and through the pulmonary artery cannula 16, provides oxygenated blood to the pulmonary artery. The oxygenator 18 can be a spiral wound sheet membrane type oxygenator or any of the hollow fiber membrane type oxygenators including, but not limited to, the CAPIOX® oxygenator manufactured by the Terumo Cardiovascular Group, the AFFINITY® oxygenator manufactured by Medtronic, the QUADROX® oxygenator manufactured by Maquet, the TANDEMLUNG™ and INSPIRE™ oxygenators manufactured by LivaNova, and others. A controller that may be used for the pump and oxygenator is described in U.S. Pat. No. 6,808,508 to Zafirelis et al.

The system 10 can be applied to a patient according to the following method. The method includes inserting a tip of the pulmonary artery cannula 16 into a right femoral vein of the patient and moving the tip through the right femoral vein until side holes of the cannula 16 in proximity to the tip are disposed in the pulmonary artery. Then, the drainage cannula 12 is inserted into the patient's vasculature, and moved through the patient's vasculature until the tip of the drainage cannula 12 is disposed in the right atrium. Then, an inlet of the pump 14 is connected to the drainage cannula 12 with inlet connecting tubing 20 to form the fluid tight connection between the drainage cannula 12 and inlet connecting tubing 20. Structures and methods for establishing the fluid tight connection between the cannula 12 and tubing 20, in accordance with the present disclosure, are described in further detail herein and illustrated in FIGS. 2A-5. Similarly, the pulmonary artery cannula 16 is connected to an outlet of the oxygenator 18 through outlet connecting tubing 22. Another piece of auxiliary connecting tubing 24 is connected between the outlet of the pump 14 and the inlet of the oxygenator 18 to form a circuit. Finally, the pump 14 and the oxygenator 18 are secured to the patient. In operation, blood received by the pump 14 from the drainage cannula 12 is pumped to the pulmonary artery through the pulmonary artery cannula 16 to provide right ventricular and respiratory support without having to bypass the heart and lungs.

Structures and methods for providing the fluid tight connectors 100, 200, 300, 400, 900 between portions of the surgical tubing 20, 22 and the cannulas 12, 16 will now be discussed in detail. For example, a proximal end of a cannula 12, 16 may be connected to a distal end of the surgical tubing 20, 22, respectively. The cannulas 12, 16 and the surgical tubing 20, 22 may be connected directly to each other, or by way of a connector disposed therebetween. As will be appreciated by those skilled in the art, it is important to remove air from the cannula 12, 16 and connecting surgical tubing 20, 22 to form a secure connection and to prevent contaminates, air bubbles, and other impurities from entering a lumen of the surgical tubing 20, 22 and/or cannula 12, 16 and being delivered to the patient. As also will be appreciated by those skilled in the art, the structures and methods for connecting portions of tubing disclosed herein can be used for other fluid collection and fluid delivery systems including, but not limited to, powered injectors, IV fluid sets, manual injectors, drug delivery devices, and others.

Figure 2A:
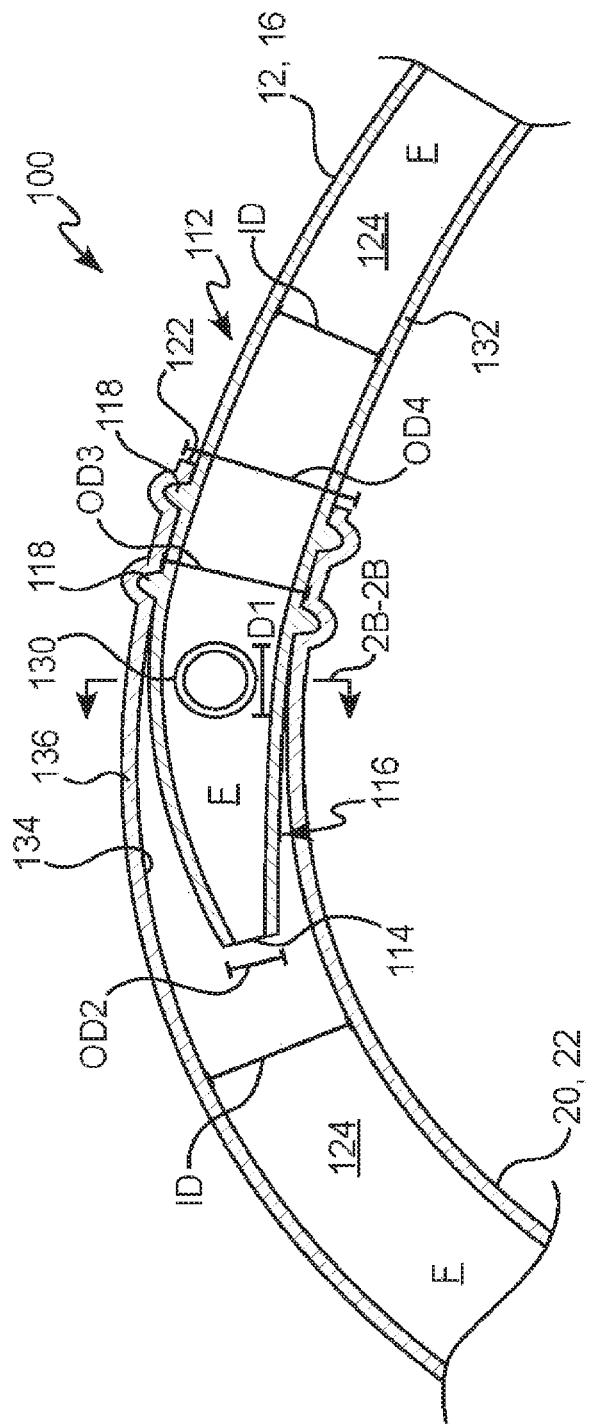
FIG. 2A is a schematic drawing of a connection between tubing portions of a cannula assembly according to some non-limiting embodiments or aspects of the disclosure.
Figure 2B:
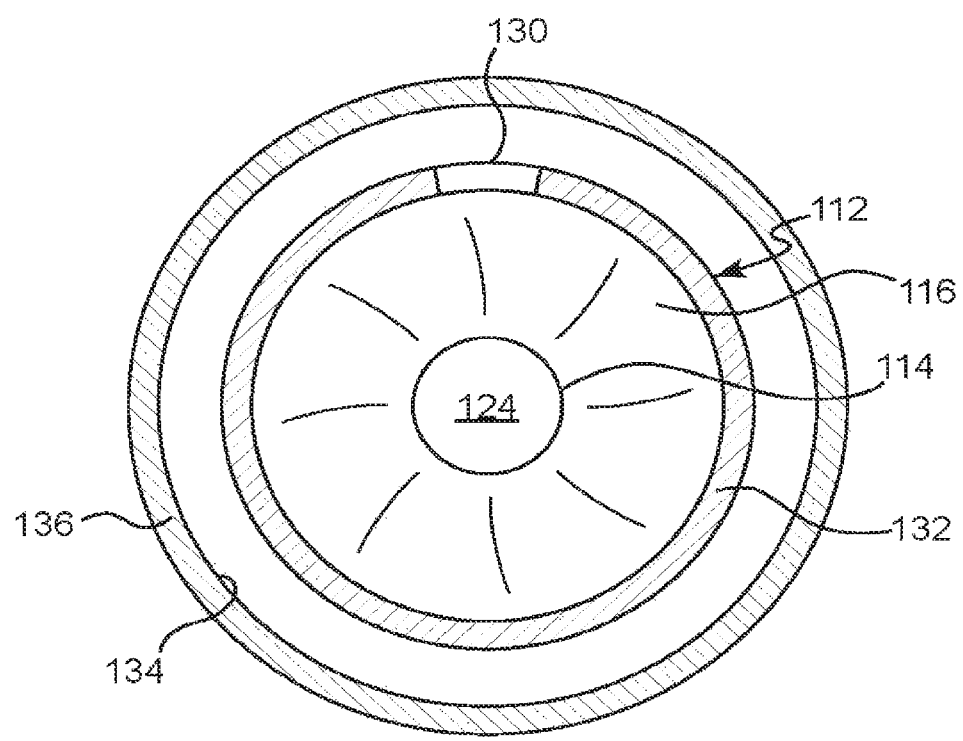
FIG. 2B is a schematic drawing of a cross sectional view of the tubing portions of FIG. 2A, taken along line 2B-2B, according to some non-limiting embodiments or aspects of the disclosure.

With reference to FIGS. 2A and 2B, an example of the connector 100, which can be configured to establish fluid communication between a portion of the cannulas 12, 16 and a portion of the surgical tubing 20, 22, is illustrated. In some non-limiting embodiments or aspects as exemplified in FIG. 2A, the connector 100 is integral with the cannula 12, 16. In other non-limiting embodiments or aspects, the connector 100 is formed as a separate component from the cannula 12, 16 and may be removably or non-removably connected to the cannula 12, 16. While FIG. 2A shows the connector 100 as being integral with the cannula 12, 16, in other non-limiting embodiments or aspects, the connector 100 may be integral with the surgical tubing 20, 22. In further non-limiting embodiments or aspects, the connector 100 may be formed as a separate component from the tubing 20, 22 and may be removably or non-removably connected to the tubing 20, 22.

The connector 100 has an outer surface 112 in close proximity with the inner surface 134 of the surgical tubing wall 136 of the surgical tubing 20, 22. For example, the outer surface 112 of the connector 100 can be in direct physical contact with the inner surface 134 of the surgical tubing wall 136 of the surgical tubing 20, 22. In some non-limiting embodiments or aspects, one or more ridges or barbs 118 of the connector wall 132 protruding from the outer surface 112 of the connector 100 may contact the inner surface 134 of the surgical wall 136. In other non-limiting embodiments or aspects, only the ridges or barbs 118 may contact the inner surface 134. When the connector 100 is connected to the inner wall 134 of the surgical tubing 20, 22, the cannula 12, 16 is in fluid communication with the surgical tubing 20, 22 through the sterile connector 100. The surgical tubing wall 136 of surgical tubing 20, 22 and cannula 12, 16 can be formed from any suitable inert flexible material, as are commonly used in construction of catheters and medical tubing, including flexible biocompatible plastic materials and metals. In some examples, surgical tubing is transparent so that the user can see the fluid level in the tubing during filling. The surgical tubing 20, 22 can have an inner diameter ID of about 6.4 mm (¼ inch) to 12.7 mm (½ inch) and an outer diameter OD of about 9.5 mm (⅜ inch) to 19.1 mm (¾ inch).

As shown in FIGS. 2A and 2B, the surgical tubing 20, 22 and cannula 12, 16 are connected by inserting an open end 114 of the connector 100 into the open end 122 of the surgical tubing 20, 22, thereby forming a continuous lumen 124 extending through the surgical tubing 20, 22, the connector 100, and the cannulas 12, 16. The continuous lumen 124 is configured to transport fluid F, such as blood.

With continued reference to FIG. 2A and 2B, surgical tubing 20, 22 and the connector 100 are structured such that, when the connector 100 is partially inserted in the surgical tubing 20, 22, the connector wall 132 defines at least one opening positioned such that fluid can be introduced to or pass through the at least one opening into the continuous lumen 124. For example, as shown in FIGS. 2A and 2B, the connector 100 can include at least one fluid port or opening 130 having a diameter D1 extending through a sidewall 132 thereof for establishing fluid communication with the continuous lumen 124. Also, the opening 130 can establish fluid communication with the continuous lumen.

With continued reference to FIG. 2A and 2B, an opening 130 is sized and positioned to allow a user to fill the lumen 124 with the fluid F to remove air from the lumen 124, which could form air bubbles in the system 10 (shown in FIG. 1), while connecting the surgical tubing 20, 22 to the connector 100. In some examples, the connector 100 includes a single circular opening 130. Desirably, the opening 130 is sized to allow a sufficient volume of the fluid F to pass into the lumen 124 through the opening 130 so that the lumen 124 can be filled relatively quickly. However, the opening 130 should also be sized and positioned so that a sufficient seal is formed between the outer surface 112 of the connector 100 and the inner surface 134 of the surgical tubing 20, 22. A size of the opening 130 can also impact a hoop strength of the connector 100. For example, a thin and long channel (e.g., Width<21 Length) may create an overhang which flexes during use and could fracture. A size of the opening 130 should be selected so that this fracture does not occur. Another consideration in determining a size of the opening 130 is surface tension. For example, if the opening 130 is too thin or narrow, drops of fluid will form on the opening 130 and will not pass through the opening 130 into the lumen 124. Accordingly, the opening 130 should be wide enough so that fluid easily passes through the opening 130. Another consideration is closing force. For example, the force required to form the connection between the surgical tubing 20, 22 and the connector 100 is dependent upon how far the connector 100 must be inserted into the surgical tubing 20, 22 to seal the opening 130. Therefore, a shorter opening 130 will require less force to close. In particular, the opening 130 should be small enough so that an average strength user can easily insert connector 100 into the surgical tubing 20, 22 without unreasonable effort.

Still referring to FIGS. 2A and 2B, in some embodiments or aspects, when used with connector 100 having an inner diameter of 9.5 mm (0.375 inch), a single circular opening 130 may have a diameter D1 of about 3.0 mm to 9.5 mm, preferably about 4.0 mm to about 7.5 mm, and an area of about 6.0 mm$^2$ to 60.0 mm$^2$, preferably about 9.0 mm$^2$ to 45.0 mm$^2$. An area of the opening 130 can be about 9% to 85% and, preferably, 12% to 65%, of an inner cross-sectional area of the connector 100.

In other embodiments or aspects, the size, shape, and number of openings can be selected based on a size of the lumen 124 or how much fluid will need to be provided to fill the lumen 124. In some embodiments or aspects, the connector 100 can include multiple openings 130, such as openings 130 arranged axially along the connector wall 132 of the connector 100. In other embodiments or aspects, the openings 130 could comprise one or more axially extending slits rather than circular openings.

With continued reference to FIGS. 2A and 2B, the open end 114 of the connector 100 can include one or more structures for securely anchoring the open end 114 of the connector 100 into the surgical tubing 20, 22. For example, as shown in FIG. 2A, the connector 100 can include a tapered nozzle or connector 116, such as a male luer connecter, for establishing a fluid connection between the cannulas 12, 16 and surgical tubing 20, 22. Other connectors, such as threaded connectors or snap fit connectors, can also be used for securing the connector 100 to the surgical tubing 20, 22. The connector 100 also can include one or more structures for preventing or restricting a user from detaching the connector 100 from the surgical tubing 20, 22. For example, as shown in FIG. 2A, the connector 100 includes one or more annular ridges or barbs 118 protruding radially outwardly from the connector wall 132 of the connector 100 configured to contact an inner surface 134 of the surgical tubing wall 136 of the surgical tubing 20, 22. The ridges or barbs 118 can extend radially outwardly from portions of the connector wall 132 of the connector 100 by about 1.0 mm to 2.0 mm, such that an outer diameter of the portion of the connector 100 including the ridge(s) is about 10.0 mm to 13.0 mm. In other embodiments or aspects, the connector 100 can include axially extending ridges, protrusions, detents and similar structures for securing the connector 100 to the surgical tubing 20, 22. In other embodiments or aspects, the surgical tubing 20, 22 can include one or more protrusions extending radially inwardly from the inner surface 134 of the surgical tubing wall 136 of the surgical tubing 20, 22 to secure the connector 100 to the surgical tubing 20, 22.

In some non-limiting embodiments or aspects, as shown in FIG. 2A, an outer diameter OD2 at the open end 114 of the connector 100 is about 10.2 mm (0.40 inches), an outer diameter OD3 of the connector 100 with the ridge 118 is 11.5 mm (0.454 in), and an outer diameter OD4 of a second barb or ridge 118, if present, with the connector wall 132 is about 12.2 mm (0.480 in).

Figure 3:
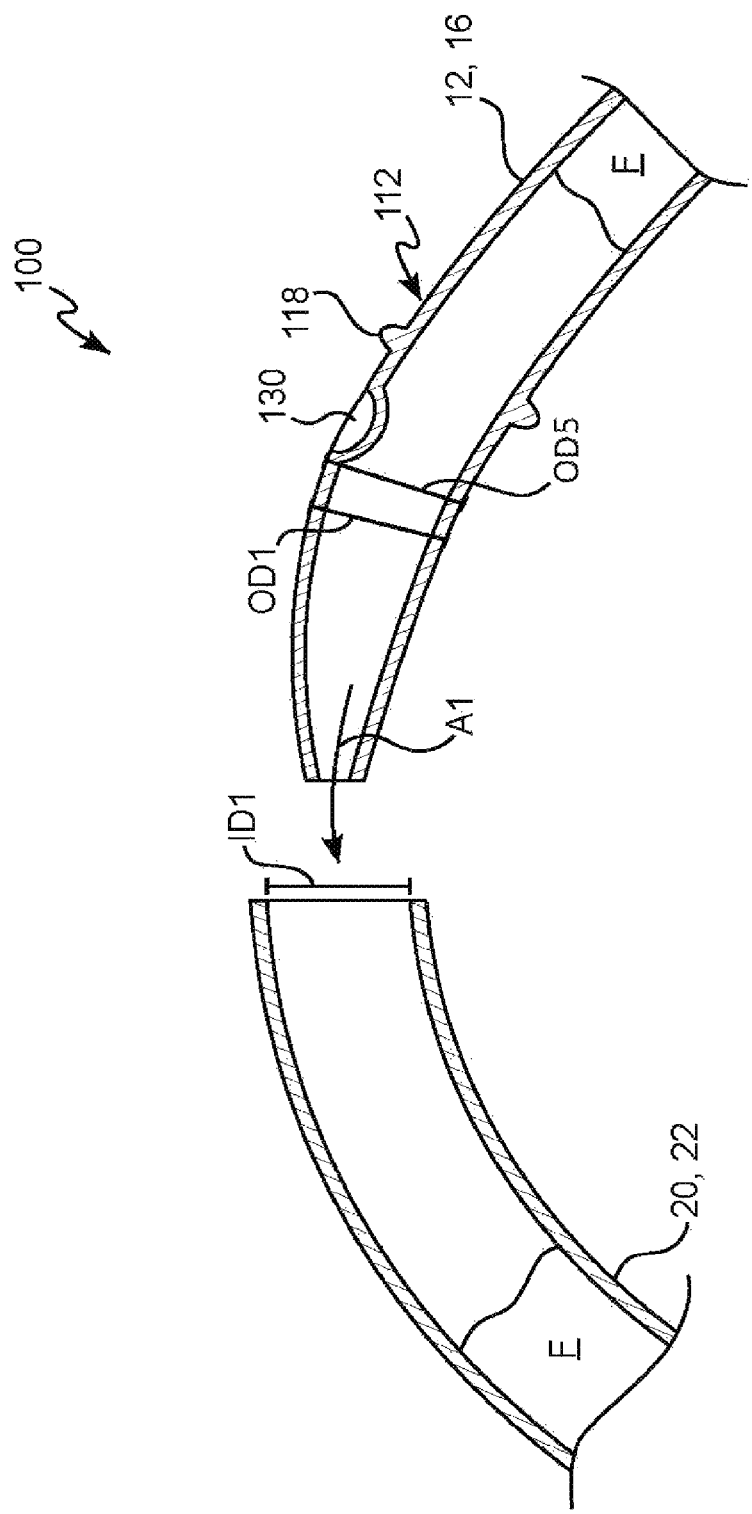
FIG. 3 is a schematic drawing of the tubing portions of FIG. 2A, prior to connecting the tubing portions together.
Figure 4:
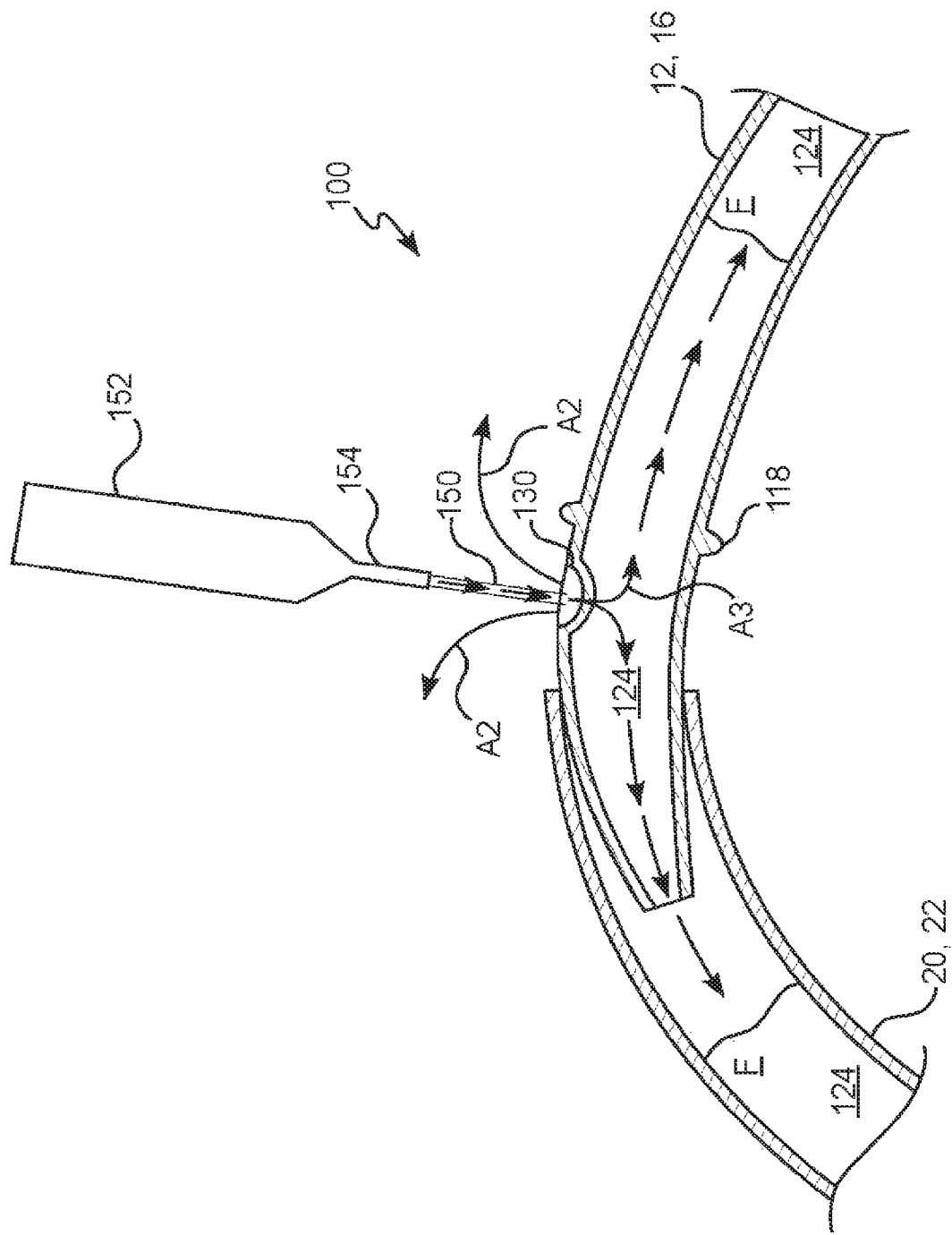
FIG. 4 is a schematic drawing of the tubing portions of FIG. 2A, with the tubing portions partially connected together.
Figure 5:
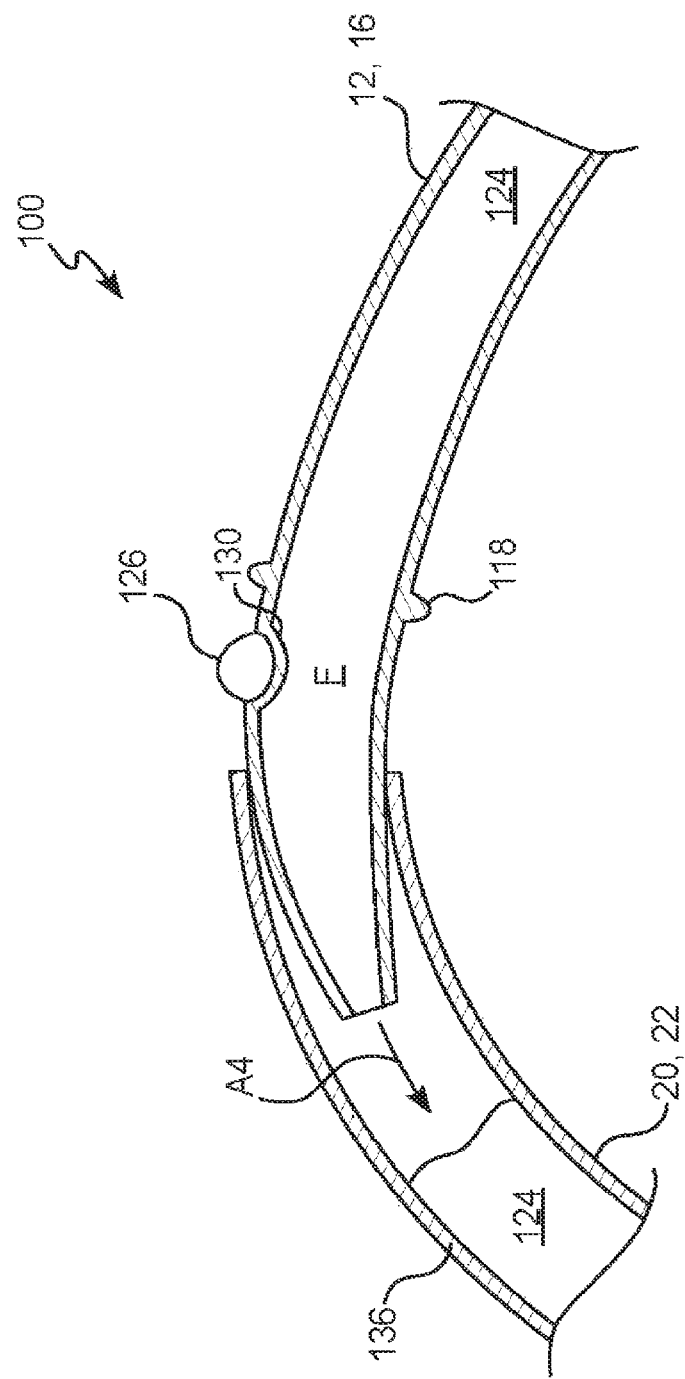
FIG. 5 is a schematic drawing of the tubing portions of FIG. 2A, with the tubing portions partially connected together and fully filled with fluid.

In order to connect the connector 100 and the surgical tubing 20, 22, a user performs the following actions, as shown in FIGS. 3-5. As described herein, the actions desirably can be performed by a single user. First, the user holds one of the tubes (e.g., either the connector 100 or the surgical tubing 20, 22) in place against a surface and, with a second hand, partially inserts the connector 100 into the surgical tubing 20, 22 in a direction shown by arrow A1, as shown in FIG. 3. The connector 100 is partially inserted in the surgical tubing 20, 22, when the surgical tubing 20, 22 covers a portion of the outer surface 112 of the connector 100, but does not cover the at least one opening 130. In this partially inserted position, as shown in FIG. 4, the at least one opening 130 is at least partially exposed, so that fluid can be applied to the lumen 124 through the at least partially exposed opening 130. In contrast, the connector 100 is fully inserted in the surgical tubing 20, 22 when the surgical tubing 20, 22 covers the at least one opening 130.

Once the surgical tubing 20, 22 and the connector 100 are in the partially inserted position, as shown in FIG. 4, the user applies or delivers a fluid F, such as saline, to the continuous lumen 124 defined by the surgical tubing 20, 22, the connector 100, and the cannula 16, 22 through the at least one opening 130 of the connector 100, such that air present in the continuous lumen 124 escapes from the lumen through the at least one opening 130 as shown by arrow A2. The fluid F can be delivered or applied as a stream 150 of fluid. The stream 150 of fluid can be provided from a syringe 152 including a nozzle 154 for directing the fluid stream 150 towards the opening 130, as shown by arrow A3. In other examples, the fluid stream 150 can be provided by a syringe including a needle capable of being inserted through the opening 130. In other examples, the fluid stream 150 can be provided by different types of injectors, pumps, and similar devices, as are known in the art.

The user continues to apply or deliver the fluid stream 150 until the lumen 124 is filled and/or over flowing with fluid, as shown in FIG. 5, thereby ensuring that no air is trapped in the lumen 124, which could form air bubbles. For example, a fluid meniscus 126 may extend slightly over the opening 130 indicating that the lumen 124 is filled. Once the lumen 124 is filled, the user pushes the connector 100 further into the surgical tubing 20, 22 in the direction of arrow A4. Inserting the connector 100 further into the surgical tubing 20, 22 decreases a volume of the lumen 124, which causes additional fluid to flow out of the at least one opening 130 until the surgical tubing 20, 22 covers the at least one opening 130. Beneficially, this continuous outflow of fluid F out of the opening 130 prevents inflow of air into the lumen 124, which creates the fluid tight sealed connection, in which, as shown in FIGS. 2A and 2B, the opening 130 is sealed against the inner surface 134 of the surgical tubing wall 136 of the surgical tubing 20, 22.

In another exemplary method of use, the wet-to-wet connection between the surgical tubing 20, 22 and connector 100 can be formed by a back-bleeding technique. In this technique, the connector 100 is partially inserted into the surgical tubing 20, 22 so that the opening 130 remains exposed, as described above. The user then unclamps a patient line or cannula, which allows fluid (e.g., blood and/or saline) pushed by the patient's blood pressure to flow into the surgical tubing 20, 22 from the connector 100. As the fluid enters the connector 100, air is pushed out of the connector 100 through the opening 130. When the surgical tubing 20, 22 is filled with fluid, such that the fluid starts to spill out of the opening 130, the user can push connector 100 fully into the surgical tubing 20, 22 to seal the connection.

Figure 6:
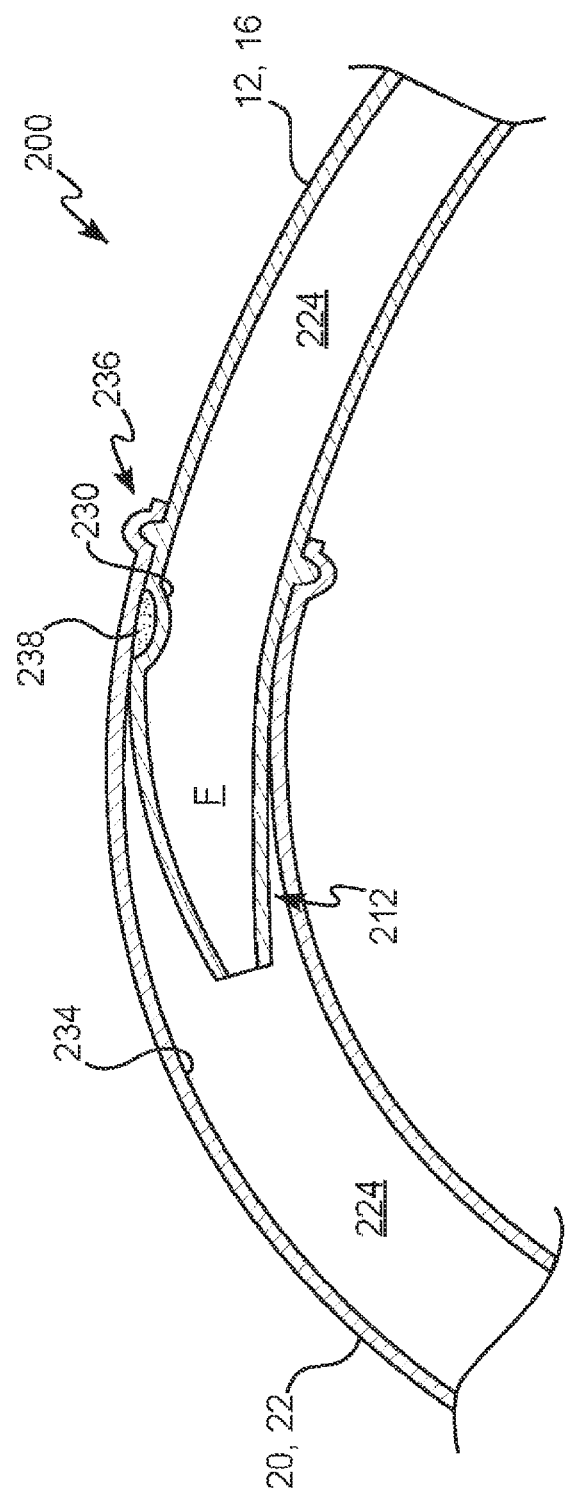
FIG. 6 is a schematic drawing of another example of a connection between tubing portions of a cannula assembly, according to some non-limiting embodiments or aspects of the disclosure.

With reference to FIG. 6, another embodiment of a connector 200 for connecting a cannula 12, 16 to surgical tubing 20, 22 is illustrated including an inner tube 212 configured to be inserted into the surgical tubing 20, 22. As in previously described examples, the connector 200 creates a sterile, fluid tight connection and can be performed easily by a single user. The connector 200 is similar to the connector 100 described above and is used in a similar manner. In particular, a tapered section 212 of the connector 200 is configured to be partially inserted into the surgical tubing 20, 22. Once in the partially inserted position, a fluid stream is applied to remove air from a continuous lumen 224 formed by the surgical tubing 20, 22 and the connector 200. However, unlike in previously described examples, the connector 200 includes a port or opening 230 covered by a septum 238. The septum 238 forms a fluid tight seal over the opening 230, which prevents fluid F in the lumen 224 from escaping through the opening 230. In some examples, using a septum 238 may be preferable so that the user does not come into contact with the fluids F in the lumen 224. The septum 238 is desirably impermeable to liquids, but is permeable to air so that air in the lumen 224 can escape through the septum 238 and opening 230. For example, the septum 238 can be formed from various hydrophobic films and fabrics, as are known in the art, including polytetrafluoroethylene (e.g., Gore-Tex®). In order to fill the lumen 224, the user inserts a needle of a syringe through the septum 238 and expels fluid F into the lumen 224 through the needle. Once the lumen 224 is filled, the user pushes the connector 200 farther into the surgical tubing 20, 22, such that the opening 230 and septum 238 are covered by the inner surface 234 of the surgical tubing wall 236 of the surgical tubing 20, 22. In other examples, the septum 238 may be impenetrable both to liquids and air. In that case, a syringe needle including a venting lumen could be inserted through the septum 238 to deliver fluid F to the lumen 224. In such an embodiment, as fluid, such as saline, is injected into the lumen 224, air is permitted to escape through the venting lumen.

Figure 7:
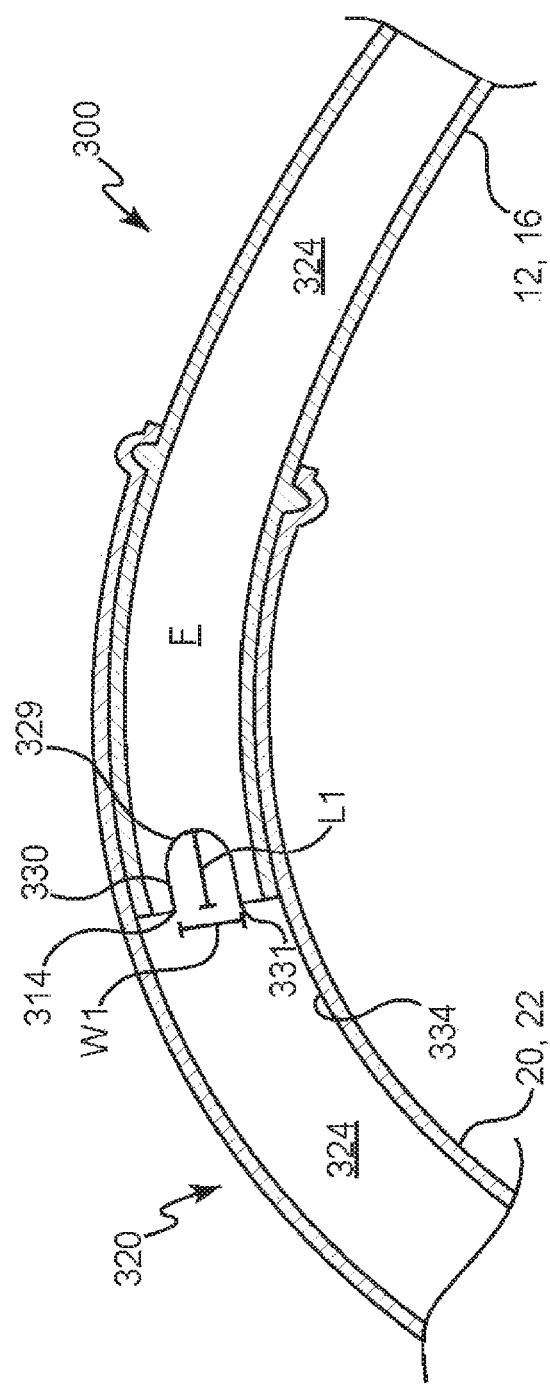
FIG. 7 is a schematic drawing of another example of a connection between tubing portions of a cannula assembly, according to some non-limiting embodiments or aspects of the disclosure.

With reference to FIG. 7, another example of a connector 300 for connecting a cannula 12, 16 to surgical tubing 20, 22 is illustrated. As in previous examples, the connector 300 is configured to be inserted into the surgical tubing 20, 22. In this example, the circular opening shown in FIGS. 2-5 is replaced with a slot, notch, or channel 330 extending axially inwardly from an open end 314 of the connector 300. As shown in FIG. 7, the channel 330 has a curved or semicircular proximal end 329 and a straight distal end 331 which is coextensive with the distal end 314 of the connector 300. As in previous examples, the channel 330 is sized so that the lumen 324 can be filled quickly, while still allowing a good seal to form between the connector 300 and the surgical tubing 20, 22. For example, the channel 330 can have a length L1 of about 4.0 mm to 11.0 mm or, preferably about 6.0 mm to 8.0 mm, and a width W1 of about 2.0 mm to 8.0 mm or, preferably about 4.0 mm to 6.0 mm. As in previous examples, an area of the channel 330 can be about 20% to about 75% and, preferably, about 33% to 60%, of an inner cross sectional area of the connector 300.

Dimensions for a number of different examples of channels 330 constructed in accordance with the current disclosure are shown in the following Table. The channels 330 are configured to be used for connecting together sections of ⅜ inch tubing having an inner diameter of 9.5 mm (0.375 inch) and an inner cross section area of about 71.0 mm² (0.11 inch). While not intending to be bound by these examples, Connectors 3-7 in the Table were found to work well during testing.

| Connector # | Length L1 (mm) | Width W1 (mm) | Area of opening (mm²) | % of cross-sectional area |
|---|---|---|---|---|
| Connector 1 | 6.2 | 7.1 | 38.7 | 54% |
| Connector 2 | 7.9 | 7.1 | 51.6 | 71% |
| Connector 3 | 6.2 | 5.8 | 32.3 | 46% |
| Connector 4 | 7.9 | 5.8 | 45.2 | 59% |
| Connector 5 | 7.0 | 5.3 | 32.3 | 48% |
| Connector 6 | 6.2 | 4.8 | 25.8 | 38% |
| Connector 7 | 7.7 | 4.8 | 38.7 | 48% |
| Connector 8 | 6.2 | 3.8 | 19.4 | 31% |
| Connector 9 | 10.2 | 5.8 | 58.1 | 78% |
| Connector 10 | 10.0 | 4.8 | 45.2 | 64% |
| Connector 11 | 4.3 | 4.8 | 19.4 | 26% |
| Connector 12 | 6.2 | 2.8 | 19.4 | 23% |

The connection between the surgical tubing 20, 22 and the connector 300 is formed in the same manner as in the previously described examples. Specifically, the user partially inserts the connector 300 into the surgical tubing 20, 22, such that at least a portion of the channel 330 remains exposed. The user then applies a stream of fluid F into the lumen 324 through the partially exposed portion of the channel 330. Once the lumen 324 is filled, such that fluid overflows through the channel 330, the user pushes the connector 300 farther into the surgical tubing 20, 22, such that the inner surface 334 of the surgical tubing wall 320 of the surgical tubing 20, 22 entirely covers the channel 330, thereby forming the fluid tight connection between the surgical tubing 20, 22 and the connector 300.

With reference to FIGS. 8A and 8B, another example of a connector 400 for connecting a cannula 12, 16 to a surgical tubing 20, 22 is illustrated. As in previous examples, the connector 400 is configured to be inserted into the surgical tubing 20, 22. In this example, the opening 430 extends through a surgical tubing wall 420 of the surgical tubing 20, 22. As shown in FIGS. 8A and 8B, the surgical tubing wall 420 can include a channel 430 extending axially inwardly from an open end 414 thereof. In other examples, as described previously, the opening 430 on the surgical tubing wall 420 can be a circular or elliptical shaped opening. In some examples, the channel 430 has a curved or semicircular proximal end 429 and a straight distal end 431 which is coextensive with the distal end 414 of the surgical tubing 20, 22. As in previous examples, the channel 430 is sized so that the lumen 424 (shown in FIG. 8B) can be filled quickly, while still allowing a good seal to form between the surgical tubing 20, 22 and the connector 400. As in previous examples, the connector 400 is inserted in the surgical tubing 20, 22 in a direction of the arrow A8 (shown in FIG. 8A). As shown in FIG. 8B, an outer surface 412 of the connector 400 seals the opening 430 to prevent fluid in the lumen 424 from passing through the opening 430. In order to enhance an integrity of the seal, the connector 400 can include a sealing structure, such as an annular ridge or protrusion 418, extending from an outer surface of the inner tube 412 which engages an inner surface of the outer tube 420. The ridge or protrusion 418 is positioned so that it can be inserted into the surgical tubing 20, 22 past the proximal end 429 of the opening 430 as shown in FIG. 8B, thereby sealing the lumen 424 from the opening 430.

Figure 9:
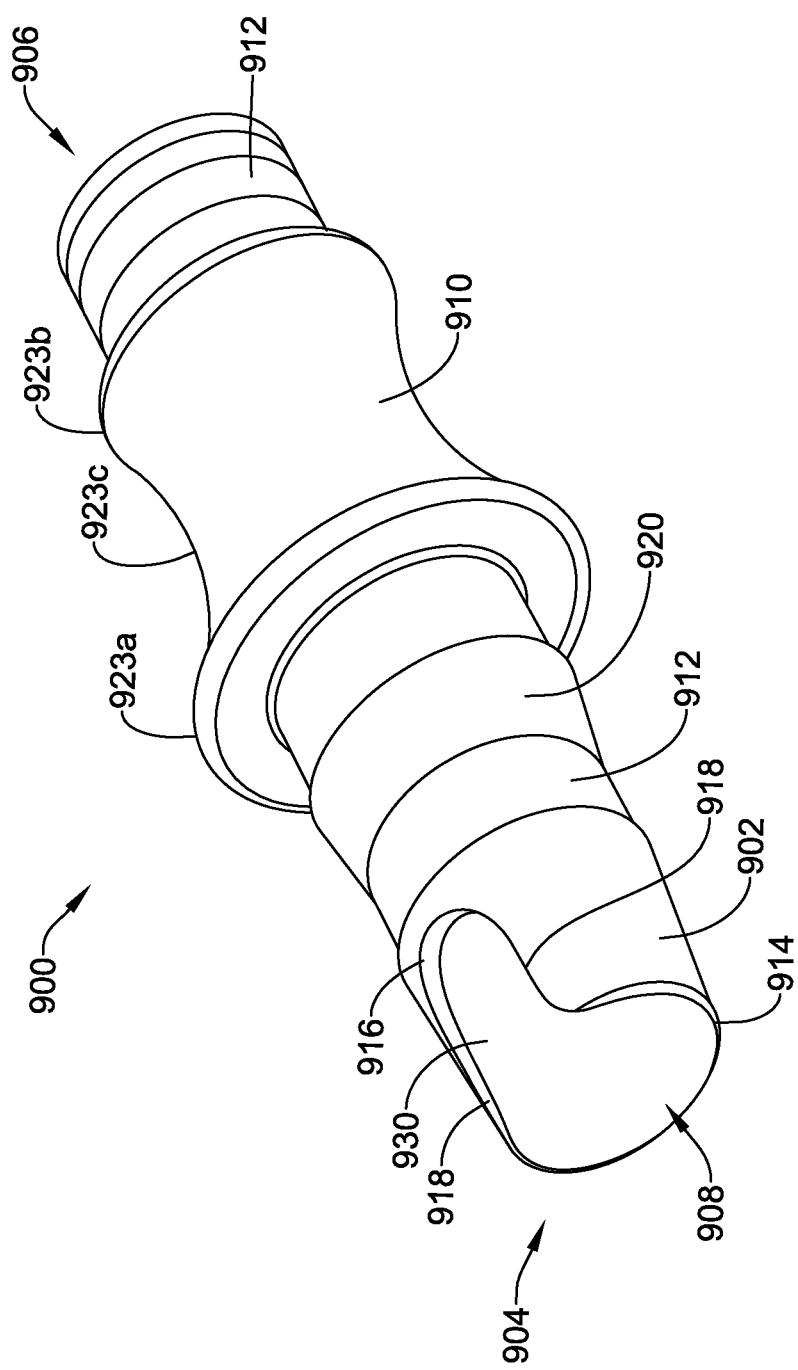
FIG. 9 is a perspective view of a connector suitable for joining tubing portions in accordance with some non-limiting embodiments or aspects of the disclosure.

With reference to FIG. 9, another example of a connector 900 for connecting a cannula 12, 16 to a surgical tubing 20, 22 is illustrated. Rather than being integrally formed with one of the cannula 12, 16 or the surgical tubing 20, 22, the connector 900 shown in FIG. 9 is formed as a separate component that is configured for removably or non-removably connecting to one of the cannula 12, 16 or the surgical tubing 20, 22.

With continued reference to FIG. 9, the connector 900 has a hollow body 902 having a first open end 904 and a second open end 906 with a lumen 908 extending between the first open end 904 and the second open end 906. In some non-limiting embodiments or aspects, the first open end 904 may be spaced apart from the second open end 906 along a longitudinal axis. The first open end 904 is sized to be received within an open end of a first tubing, such as one of the surgical tubing 20, 22 (shown in FIG. 10). Similarly, the second open end 906 is sized to be received within an open end of a second tubing, such as one of the cannulas 12, 16 (shown in FIG. 10).

With continued reference to FIG. 9, the body 902 has at least one channel 930, similar to the at least one channel 330 described herein with reference to FIG. 7. The at least one channel 930 extends through a sidewall of the hollow body 902 proximate to the first open end 904. The at least one channel 930 may be recessed axially from a terminal surface 914 of the first open end 904. The channel 930 is sized and positioned to allow a user to fill the lumen 908 with fluid to remove air from the lumen 908 during connection of the connector 900 with the first tubing, such as one of the surgical tubing 20, 22 (shown in FIG. 10). In some non-limiting embodiments or aspects, the connector 900 includes a U-shaped channel 930 that is sized to allow a sufficient volume of the fluid to pass into the lumen 908 through the channel 930 so that the lumen 908 can be filled relatively quickly. The channel 930 may have a curved end 916 and a pair of sides 918 connecting the curved end 916 to the terminal surface 914 of the first open end 904.

A size of the channel 930 can also impact a hoop strength of the connector 900. Another consideration in determining a size of the channel 930 is surface tension. For example, if the channel 930 is too thin or narrow, drops of fluid will form on the channel 930 and will not pass through the channel 930 into the lumen 908. Accordingly, the channel 930 should be wide enough so that fluid easily passes through the channel 930. Another consideration is closing force. For example, the force required to form the connection between the surgical tubing 20, 22 and the connector 900 is dependent upon how far the connector 900 must be inserted into the surgical tubing 20, 22 to seal the channel 930. Therefore, a shorter channel 930 will require less force to close. In particular, the channel 930 should be small enough so that an average strength user can easily insert connector 900 into the surgical tubing 20, 22 without unreasonable effort. In some non-limiting embodiments or aspects, a width of the at least one channel 930 is from 60% to 100% of a length of the at least one channel 930. In other embodiments or aspects, the size, shape, and number of channels 930 can be selected based on a size of the lumen 908 or how much fluid will need to be provided to fill the lumen 908. In some embodiments or aspects, the connector 900 can include multiple channels 930, such as channels 930 arranged circumferentially around the first open end 904.

Figure 10:
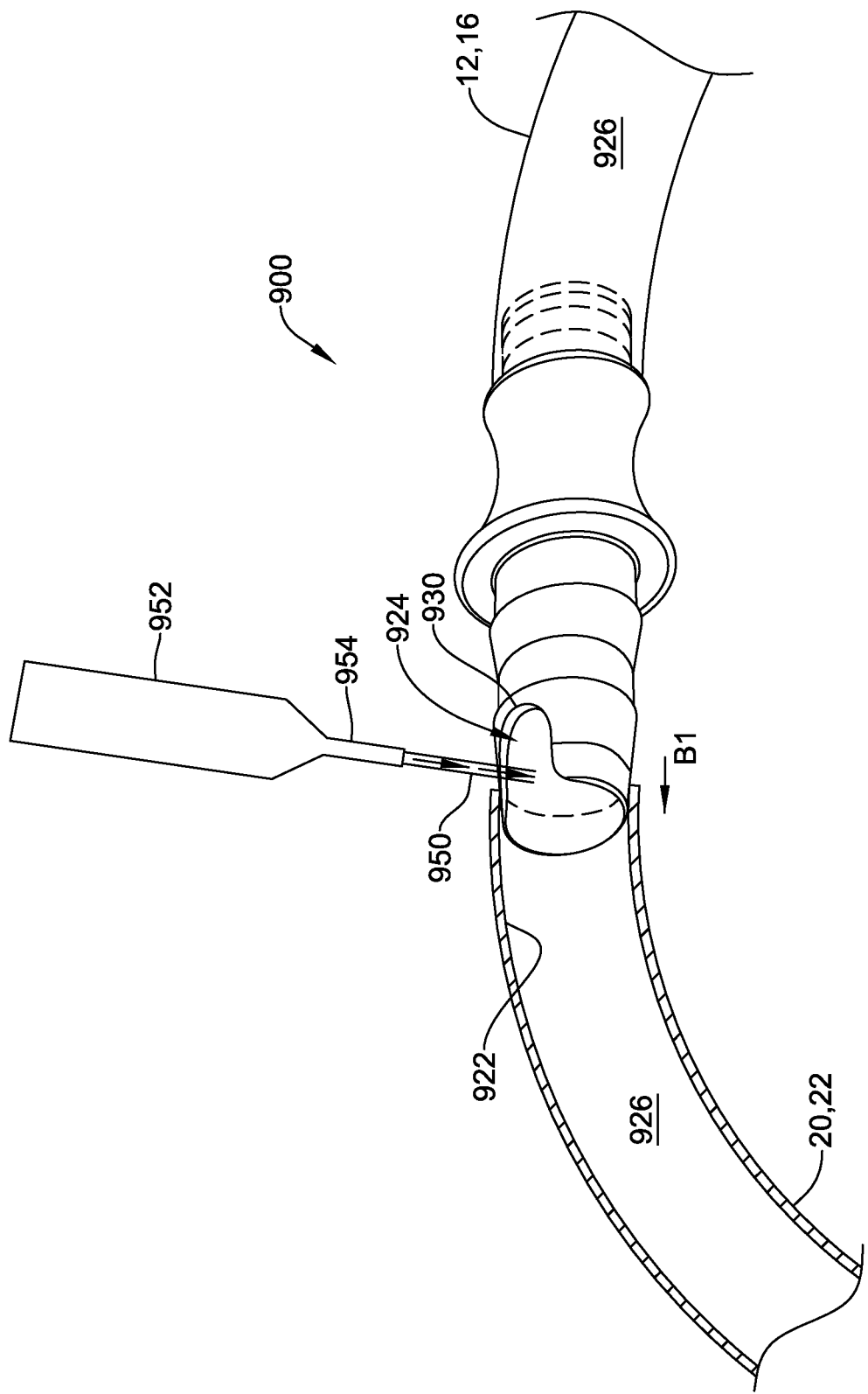
FIG. 10 is a perspective view of the connector of FIG. 9 shown in use with tubing portions, with the connector partially connecting the tubing portions.

With continued reference to FIG. 9, the first and second open ends 904, 906 of the connector 900 can include one or more structures for securely anchoring the open ends 904, 906 to the surgical tubing 20, 22 or the cannulas 12, 16. For example, the connector 900 can include a tapered portion 912 at the first and second open ends 904, 906 to facilitate insertion of the first and second open ends 904, 906 into the open ends of the cannulas 12, 16 or surgical tubing 20, 22. Other connectors, such as threaded connectors or snap fit connectors, can also be used for securing the connector 900 to the surgical tubing 20, 22. In various embodiments or aspects, the second open end 906 may be removably or non-removably connected to the open end of the cannulas 12, 16, such as shown in FIG. 10. For example, the second open end 906 may be connected to the open end of the cannulas 12, 16 using adhesive or by being molded integrally with the open end of one of the cannulas 12, 16. The first open end 904 of the connector 900 may have one or more structures for preventing or restricting a user from detaching the connector 900 from the surgical tubing 20, 22. For example, as shown in FIG. 9, the connector 900 includes one or more annular ridges or barbs 920 protruding radially outwardly from the outer surface of the body 902. The one or more ridges or barbs 920 are configured to contact an inner surface 922 of the surgical tubing wall of the surgical tubing 20, 22 (shown in FIG. 10).

In some non-limiting embodiments or aspects, the connector 900 has a gripping portion 910 configured for being grasped by the user's fingers during handling of the connector 900. The gripping portion 910 is positioned between the first open end 904 and the second open end 906. The gripping portion 910 may have a curved shape with a first end 923*a* having a first diameter, a second end 923*b* having a second diameter, and an intermediate portion 923*c* between the first end 923*a* and the second end 923*c*. The intermediate portion 923*c* may have a third diameter less than the first diameter and the second diameter.

Figure 11:
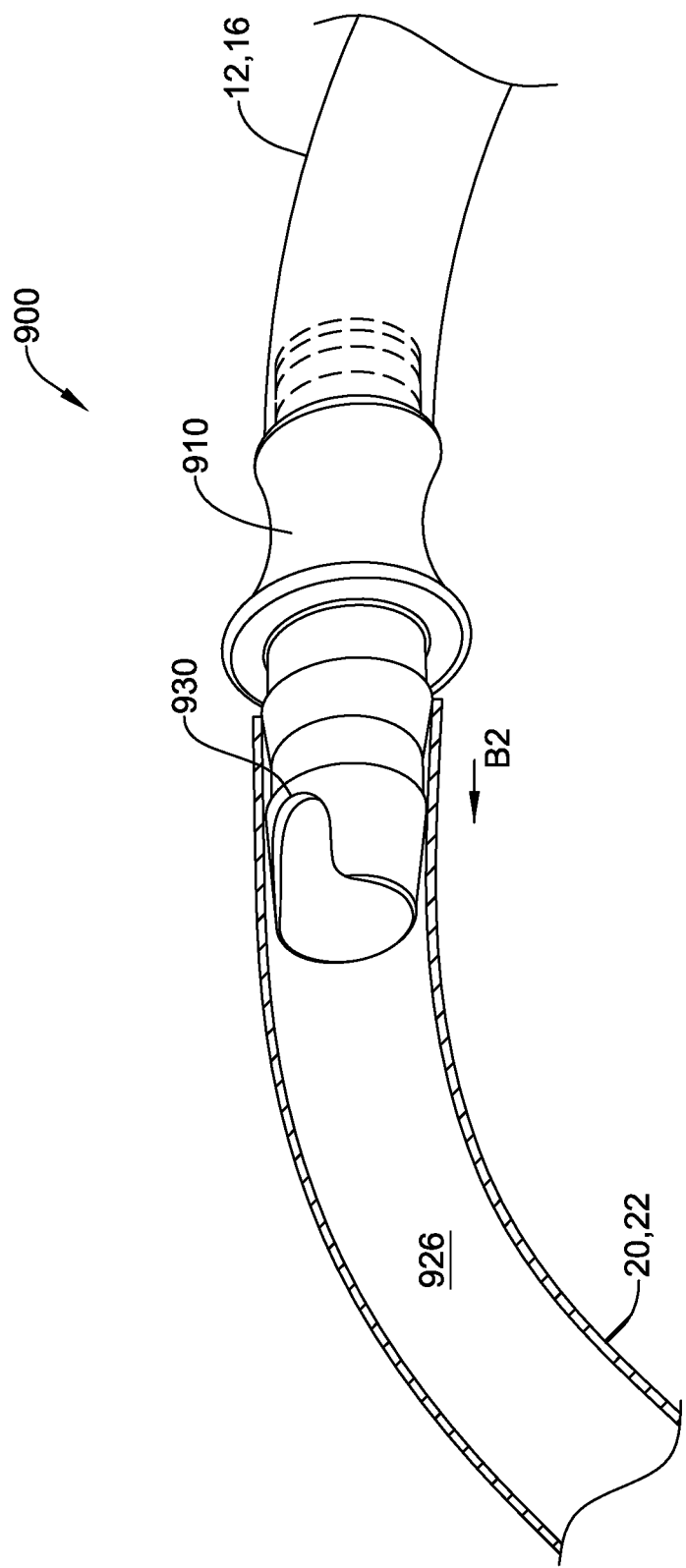
FIG. 11 is a perspective view of the connector of FIG. 9 shown in use with tubing portions, with the connector fully connecting the tubing portions.

In order to connect the first open end 904 of the connector 900 and the surgical tubing 20, 22, a user performs the following actions, as shown in FIGS. 10-11. As shown in FIGS. 10-11, the second open end 906 is connected to the cannula 12, 16. As described herein, the actions desirably can be performed by a single user. First, the user holds either the connector 900 or the surgical tubing 20, 22 in place with one hand and, with a second hand, partially inserts the first open end 904 of the connector 100 into the open end of the surgical tubing 20, 22 in a direction shown by arrow B1, as shown in FIG. 10. The connector 900 is partially inserted in the surgical tubing 20, 22, when the surgical tubing 20, 22 covers a portion of the outer surface at the terminal end of the first open end 904 of the connector 900, but does not cover the at least one channel 930. In this partially inserted position, as shown in FIG. 10, the at least one channel 930 and a terminal surface of the open end of the surgical tubing 20, 22 define an opening 924 positioned so that fluid can pass through the opening 924 into or out of the lumen 908 of the connector 900 and the lumen 926 of the surgical tubing 20, 22 and the cannula 12, 16. The opening 924 may have a surface area of 15.0 mm$^2$ to 60.0 mm$^2$. In some embodiments or aspects, the opening 924 may have a surface area that is 20% to 75% of a cross-sectional area of the surgical tubing 20, 22.

Once the surgical tubing 20, 22 and the first open end 904 of the connector 900 are in the partially inserted position, as shown in FIG. 10, the user applies or delivers a fluid F, such as saline, to fill the lumen 908 of the connector 900 and the lumen 926 of the surgical tubing 20, 22 and the cannula 12, 16. The fluid F can be delivered from a syringe 952 including a nozzle 954 for directing a fluid stream 950 towards the opening 924. In other examples, the fluid stream 950 can be provided by a syringe including a needle capable of being inserted through the opening 924. In other examples, the fluid stream 950 can be provided by different types of injectors, pumps, and similar devices, as are known in the art.

The user continues to apply or deliver the fluid stream 950 until the lumens of the surgical tubing 20, 22, the connector 900, and the cannula 12, 16 are filled and/or over flowing with fluid, thereby ensuring that no air is trapped. For example, a fluid meniscus may extend slightly over the opening 924 indicating that the lumens of the surgical tubing 20, 22, the connector 900, and the cannula 12, 16 are filled. Once the lumens are filled, the user pushes the first open end 904 of the connector 900 further into the surgical tubing 20, 22 in the direction of arrow B2 shown in FIG. 11. Inserting the connector 900 further into the surgical tubing 20, 22 decreases a volume of the lumen, which causes additional fluid to flow out of the at least one opening 924 until the surgical tubing 20, 22 covers the at least one opening 924. Beneficially, this continuous outflow of fluid out of the opening 924 prevents inflow of air into the lumen, which creates the fluid tight sealed connection, in which the opening 924 is sealed against the inner surface of the surgical tubing 20, 22.

While specific embodiments or aspects have been described in detail in the foregoing, it will be appreciated by those skilled in the art that various modifications and alternatives to those details could be developed in light of the overall teachings of the disclosure. Accordingly, the particular arrangements disclosed are meant to be illustrative only and not limiting as to the scope of disclosure. Further, although the embodiments disclosed herein have been described in detail for the purpose of illustration based on what is currently considered to be the most practical and preferred embodiments or aspects, it is to be understood that such detail is solely for that purpose and that the disclosure is not limited to the disclosed embodiments or aspects, but, on the contrary, is intended to cover modifications and equivalent arrangements that are within the spirit and scope of the appended claims. For example, it is to be understood that the present disclosure contemplates that, to the extent possible, one or more features of any embodiment or aspect can be combined with one or more features of any other embodiment or aspect.

What is claimed is:

1. A connector comprising:
   a hollow body having a first open end spaced apart from a second open end with a lumen extending between the first open end and the second open end;
   a gripping portion between the first open end and the second open end of the hollow body, the gripping portion having a first end having a first diameter, a second end having a second diameter, and an intermediate portion between the first end and the second end of the gripping portion, the intermediate portion having a third diameter less than the first diameter and the second diameter; and
   a single U-shaped channel extending through a sidewall of the hollow body, the single channel being recessed axially from a terminal surface of the first open end, wherein the terminal surface of the first open end defines a curve of at least 180 degrees in a plane, wherein sides of the U-shaped channel intersect ends of the curve of the terminal surface,
   wherein the first open end is sized to be received within an open end of a first tubing,
   wherein, when the first open end is partially inserted into the open end of the first tubing, the single U-shaped channel and a terminal surface of the open end of the first tubing define an opening positioned so that fluid passes through the opening into or out of the lumen, and fluid delivered through the opening fills the lumen of the hollow body and the first tubing, and
   wherein, when the first open end is fully inserted into the open end of the first tubing, the single U-shaped channel is covered by an inner surface of the first tubing to cover the opening.

2. The connector of claim 1, wherein a width of the single channel is from 60% to 100% of a length of the single channel.

3. The connector of claim 1, wherein an area of the at least one opening, when the first open end of the connector is partially inserted into the open end of the first tubing, is from 15.0 mm$^2$ to 60.0 mm$^2$.

4. The connector of claim 1, wherein an area of the at least one opening, when the first open end of the connector is partially inserted into the open end of the first tubing, is from 20% to 75% of a cross-sectional area of the first tube.

5. The connector of claim 1, wherein the first open end comprises a first tapered portion configured to be inserted in the open end of the first tubing and the second open end comprises a second tapered portion sized to be received within an open end of a second tubing.

6. The connector of claim 5, wherein each of the first tapered portion and the second tapered portion comprises one or more of a luer connector, a threaded connector, and a snap fit connector.

7. The connector of claim 1, further comprising at least one ridge or barb protruding outward relative to an outer surface of the hollow body.

8. The connector of claim 7, wherein the at least one ridge or barb is a plurality of ridges or barbs axially spaced from each other along a length of the hollow body between the first open end and the second open end.

9. A cannula assembly for providing a sterile connection between tubing portions of the assembly, the cannula assembly comprising:
   a first tubing portion defining a tubing lumen and comprising an open end;
   a second tubing portion comprising an open end; and
   a connector having a hollow body with a first open end spaced apart from a second open end and a lumen extending between the first open end and the second open end of the connector,
   the connector including a gripping portion between the first open end and the second open end of the connector, the gripping portion having a first end having a first diameter, a second end having a second diameter, and an intermediate portion between the first end and the second end of the gripping portion, the intermediate portion having a third diameter less than the first diameter and the second diameter;
   wherein the first open end is sized to be received within the open end of the first tubing portion,
   wherein the second open end is sized to be received within the open end of the second tubing portion,
   wherein a single U-shaped channel extends through a sidewall of the hollow body, the single channel being recessed axially from a terminal surface of the first open end, the terminal surface defining a curve of at least 180 degrees in a plane, wherein sides of the U-shaped channel intersect ends of the curve of the terminal surface,
   wherein, when the first open end of the connector is partially inserted into the open end of the first tubing portion, the single U-shaped channel and the terminal surface of the open end of the first tubing portion define an opening positioned so that fluid passes through the opening into or out of the lumen of the connector and the tubing lumen, and fluid delivered through the opening fills the lumen of the hollow body and the first tubing;

wherein, when the first open end is fully inserted into the open end of the first tubing, the single U-shaped channel is covered by an inner surface of the first tubing to cover the opening.

10. The cannula assembly of claim 9, wherein a width of the single channel is from 60% to 100% of a length of the single channel.

11. The cannula assembly of claim 9, wherein an area of the at least one opening, when the first open end of the connector is partially inserted into the open end of the first tubing, is from 15.0 mm$^2$ to 60.0 mm$^2$ and the area is from 20% to 75% of a cross-sectional area of the first tube.

12. A tubing assembly comprising:
a first tubing portion defining a tubing lumen and comprising an open end; and
a connector having a hollow body with a first open end and a lumen extending therethrough,
the connector including a gripping portion between the first open end and a second end of the connector, the gripping portion having a first end having a first diameter, a second end having a second diameter, and an intermediate portion between the first end and the second end of the gripping portion, the intermediate portion having a third diameter less than the first diameter and the second diameter;

wherein the first open end of the connector is sized to be received within the open end of the first tubing;

wherein a single U-shaped channel extends through a sidewall of the hollow body, the single channel being recessed axially from a terminal surface of the first open end, the terminal surface defining a curve of at least 180 degrees in a plane, wherein sides of the U-shaped channel intersect ends of the curve of the terminal surface, wherein, when the first open end of the connector is partially inserted into the open end of the first tubing, the single U-shaped channel and a terminal surface of the open end of the first tubing define an opening positioned so that fluid passes through the opening into or out of the lumen of the connector and the tubing lumen, and wherein, when the first open end of the connector is fully inserted into the open end of the first tubing, the single U-shaped channel is covered by an inner surface of the first tubing to cover the opening.

13. The tubing assembly of claim 12, wherein a width of the single channel is from 60% to 100% of a length of the single channel.

14. The tubing assembly of claim 12, wherein an area of the opening, when the first open end of the connector is partially inserted into the open end of the first tubing, is from 15.0 mm$^2$ to 60.0 mm$^2$ and the area is from 20% to 75% of a cross-sectional area of the first tube.

* * * * *